United States Patent
Dozol et al.

[11] Patent Number: 5,926,687
[45] Date of Patent: Jul. 20, 1999

[54] CROWN CALIX |4| ARENES, THEIR PREPARATION PROCESS AND THEIR USE FOR THE SELECTIVE EXTRACTION OF CESIUM AND ACTINIDES

[75] Inventors: Jean-François Dozol, Pierrevert; Hélène Rouquette, Nanosque, both of France; Rocco Ungaro; Alessandro Casnati, both of Parma, Italy

[73] Assignee: Commissariat a l'Energie Atomique, Paris, France

[21] Appl. No.: 08/535,015

[22] PCT Filed: Apr. 18, 1994

[86] PCT No.: PCT/FR94/00432

§ 371 Date: Oct. 4, 1995

§ 102(e) Date: Oct. 4, 1995

[87] PCT Pub. No.: WO94/24138

PCT Pub. Date: Oct. 27, 1994

[30] Foreign Application Priority Data

Apr. 19, 1993 [FR] France .................................. 93/04566

[51] Int. Cl.⁶ .................................................... B01D 11/00
[52] U.S. Cl. ................................... 423/8; 423/9; 210/681; 210/682; 210/638; 210/643; 546/255; 549/354
[58] Field of Search ........................... 423/8, 9; 210/682, 210/638, 643; 546/255; 549/354

[56] References Cited

U.S. PATENT DOCUMENTS

| | | | |
|---|---|---|---|
| 4,477,377 | 10/1984 | Izatt et al. | 252/631 |
| 5,210,216 | 5/1993 | Harris et al. | 548/518 |
| 5,412,114 | 5/1995 | Shinkai et al. | 549/354 |
| 5,607,591 | 3/1997 | Dozol et al. | 210/638 |

FOREIGN PATENT DOCUMENTS

WO 93/12428  6/1993  WIPO .............................. G01N 33/84

OTHER PUBLICATIONS

Journal of the American Chemical Society, vol. 12, 1990, Gaston, PA US, pp. 6979–6985, E. Ghidini et al. Complexation of Alkali Metal Cations by Conformationally Rigid, Stereoisomeric Calix(4) Arene Crown Ethers.

Yamamoto, H, et al. Molecular Design of Calix [4] Arene–Based Sodium Selective Electrodes Which Show Remarkably High $10^{5.0}$–$10^{5.3}$ Sodium/Potassium Selectivity, Chemistry Letters, 1994 pp. 1115–1118.

*Primary Examiner*—Ngoclan Mai
*Attorney, Agent, or Firm*—Pearne, Gordon, McCoy & Granger LLP

[57] ABSTRACT

The invention relates to crown calix|4|arenes, their preparation process and their use for the selective extraction of cesium and actinides. These crown calix|4|arenes comply with the formula:

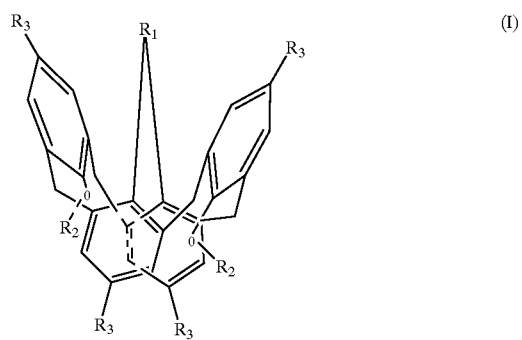

in which $R_1$ represents a group of formula $X(C_2H_4X)_m$ and $X(C_2H_4X)_n$, $YX(C_2H_4X)_n$ with X=O or $N(R_4)$, m=3, 4, 5 or 6, Y=cycloalkylene or arylene and n=1, 2 or 3. These crown|4|arenes, whose benzene nuclei are optionally substituted by alkyl groups, can be used as extractants, e.g. in liquid membrane form, for separating cesium from acid solutions containing sodium in a large quantity compared with the cesium quantity, e.g. irradiated fuel reprocessing plant effluents.

14 Claims, No Drawings

CROWN CALIX [4] ARENES, THEIR PREPARATION PROCESS AND THEIR USE FOR THE SELECTIVE EXTRACTION OF CESIUM AND ACTINIDES

The present invention relates to crown calix[4]arenes, their preparation process and their use for the selective extraction of cesium and actinides.

More specifically, it relates to crown calix[4]arenes able to selectively extract the cesium and actinides present in trace state in acid solutions which may or may not have high cation concentrations, such as the aqueous effluents coming from irradiated nuclear fuel reprocessing installations or irradiated fuel dissolving solutions.

In these effluents cesium 137 is one of the most noxious fission products as a result of its long half life (30 years). It is therefore of interest to selective eliminate it from the liquid effluents coming from the reprocessing plants, particularly concentrates of evaporators and acid solutions which may or may not have a high salinity more particularly due to the presence of sodium nitrate.

In view of the very similar chemical properties of sodium and cesium, it is extremely difficult to selectively extract the cesium present in these effluents, with a concentration generally below $10^{-6}$ mole/l, whereas the sodium concentration is approximately 4 mole/l.

In order to solve this problem, consideration has been given to the extraction of the cesium by means of macrocyclic ligands such as the para tert-butyl-calixarenes described in U.S. Pat. No. 4,477,377. The para tert-butyl-calixarenes used are the tetramer, hexamer and octamer and the best results are obtained with the hexamer and octamer, the tetramer not having a very good selectivity for separating the cesium from the potassium. This cesium extraction procedure is of interest, but suffers from the main disadvantage of only being applicable to the treatment of basic aqueous solutions, whereas most of the effluents resulting from reprocessing are acid solutions.

Other macrocyclic ligands such as crown ethers are also used for this purpose, as described in "Selective Extraction of Cesium from Acidic Nitrate Solutions with Didodecylnaphthalene sulphonic acid synergized with biz(tert-butylbenzo)-21 crown 7" by W. J. McDowell et al, Anal. Chem., 1992, 64, pp 3013–3017, but they have a low selectivity with respect to cesium.

The present invention specifically relates to novel calixarenes making it possible to selectively extract cesium from acid solutions and separate it from sodium with a good efficiency.

According to the invention, the calixarenes are crown calix[4]arenes of formula:

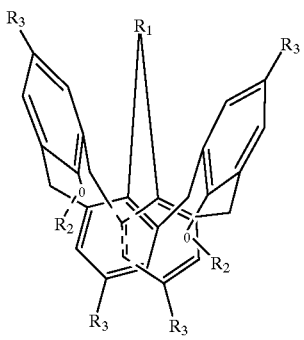

in which $R_1$ represents a group of formula $X(CH_2CH_2X)_m$ or of formula $X(CH_2CH_2X)_n YX(CH_2CH_2X)_n$ in which X represents O and/or $N(R_4)$ with $R_4$ being a hydrogen atom or an alkyl group, Y representing a cycloalkylene or arylene group optionally having a heteroatom, m being equal to 3, 4, 5 or 6 and n equal to 1, 2 or 3, $R_2$ represents a hydrogen atom, an alkyl group, a group of formula

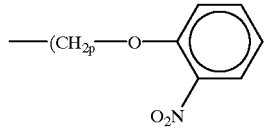

with p being equal to 5, 6, 7, or 8, $-CH_2-CH_2OH$ or $-CH_2COR_5$ with $R_5$ representing a group of formula $OR_6$, $NR_6R_7$ or $R_6$ in which $R_6$ and $R_7$, which can be the same or different, represent a hydrogen atom, an alkyl group or an aryl group, the two $R_2$ possibly being different, and $R_3$ represents a hydrogen atom or a $C_1$ to $C_3$ alkyl group.

In the above formula, the alkyl groups used for $R_2$, $R_4$, $R_6$ and $R_6$ can be straight or branched and are not necessarily identical, particularly for $R_2$.

In general, the alkyl groups used for $R_4$, $R_6$ and $R_7$ are alkyl groups having 1 to 4 carbon atoms. However, the alkyl groups used for $R_2$ can also have carbon atoms, e.g. 1 to 12 and preferably 1 to 8 carbon atoms.

The aryl groups used for $R_6$ and $R_7$ generally have 6 to 14 carbon atoms. As examples of such groups, reference can be made to phenyl and naphthyl groups.

In the formula given hereinbefore, the term "cycloalkylene" group is understood to mean a divalent group derived from a cyclic hydrocarbon by removing a hydrogen atom at each of two carbon atoms of the cycle. As an example of such a group, reference can be made to the cyclohexylene group. The cycloalkylene groups used for Y generally have 6 to 12 carbon atoms.

The term "arylene" group is understood to mean a group derived from an aromatic hydrocarbon having one or more aromatic nuclei or a heterocyclic nucleus having a heteroatom such as O, S or N, by removing a hydrogen atom at each of the two carbon atoms of the cycle.

As examples of such groups, reference can be made to the phenylene, naphthylene, benzylene, pyridylene and thienylene groups.

In the $R_1$ member, the X can represent hydrogen atoms, which can be partly or totally replaced by nitrogen atoms $NR^4$.

The calixarenes according to the invention are very different from the calixarenes used in U.S. Pat. No. 4,477,377. Thus, the latter document uses calixarenes having on each benzene nucleus a hydroxyl group and a tertbutyl group and these calixarenes only have a single macrocycle.

However, in the calixarenes according to the invention, there are two cycles, respectively constituted by a first cycle corresponding to all the benzene nuclei interconnected by $CH_2$ groups, and a second cycle formed by a crown ether or crown aza bridge between two diametrically opposite benzene nuclei. Preferably, the second cycle is formed by a crown ether bridge of formula $O(CH_2CH_2O)_m$ with m=5 or 6.

As a result of their particular structure, the calixarenes according to the invention combine the crown ether complexing properties with respect to alkalis with properties of the calixarenes, i.e. a high sensitivity imposed by the rigid structure of the cavity and a high lipophilic character making the molecule particularly interesting for use in a supported liquid membrane.

In the calixarenes according to the invention, $R_3$ advantageously represents a hydrogen atom.

When $R_2$ is not an alkyl group, it can e.g. be the —$CH_2CH_2OH$ or —$CH_2COOCH_2CH_3$ group.

The calixarenes of formula I with $R_2$ representing a hydrogen atom can be prepared by a process consisting of reacting a calix|4|arene of formula:

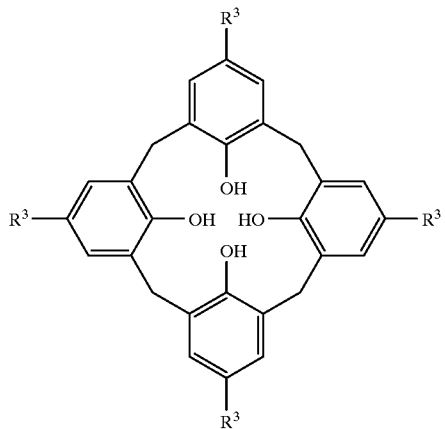

(II)

in which $R_3$ has the meaning given hereinbefore, with a compound complying with one of the formulas:

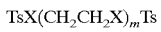 (III)

and

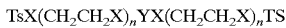 (IV)

in which X, m, Y and n have the meanings given hereinbefore and Ts represents $CH_3$—$C_6H_4$—$SO_2$ and separating the crown calix|4|arene obtained from the reaction medium.

The crown calix|4|arenes according to formula (I) with $R_2$ differing from a hydrogen atom can be prepared by a process comprising two stages from the calix|4|arene of formula (II) by performing a substitution stage for the same using $R_2$ groups and a formation stage of the crown ether or crown aza bridge $R_1$.

According to a first embodiment of said process, it comprises the following stages:

a) reacting a calix|4|arene of formula:

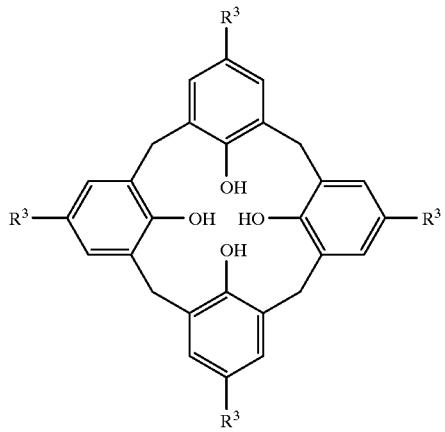

(II)

in which $R_3$ has the meaning given hereinbefore, with a halide of formula $R_2Z$, in which $R_2$ has the meaning given hereinbefore and Z is a halogen atom, b) reacting the calix|4|arene obtained in stage a) with a compound complying with one of the following formulas:

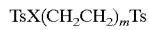 (III)

and

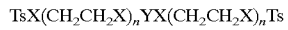 (IV)

in which X, m, Y, n and Ts have the meanings given hereinbefore and c) separating the crown calix|4|arene obtained from the reaction medium.

This process, called process A, is diagrammatically illustrated hereinafter.

With this process, one starts with compound 1 of formula (II) which is partly substituted by $R_2$ to obtain compound 2 and then formation takes place of the crown aza or crown ether bridge in order to obtain compound 4, i.e. the crown calix|4|arene of formula (I).

According to a second embodiment, the process comprises the following stages:

a) Reacting a calix|4|arene of formula:

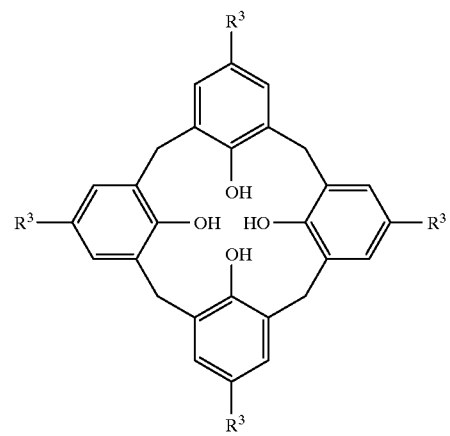

(II)

in which $R_3$ has the meaning given hereinbefore, with a compound complying with one of the following formulas:

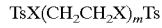 (III)

and

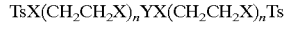 (IV)

in which X, m, Y, Ts and n have the meanings given hereinbefore, b) reacting the crown calix|4|arene obtained in stage a) with a halide of formula $R_2Z$, in which $R_2$ has the meaning given hereinbefore and Z is a halogen atom, and c) separating the crown calix|4|arene of formula (I) obtained in this way from the reaction medium.

This process, called process B, is also illustrated hereinafter. In this case, one once again starts with the compound 1, but then the crown ether or crown aza bridge $R_1$ is formed in order to obtain compound 3, which is then substituted by $R_2$ to obtain compound 4.

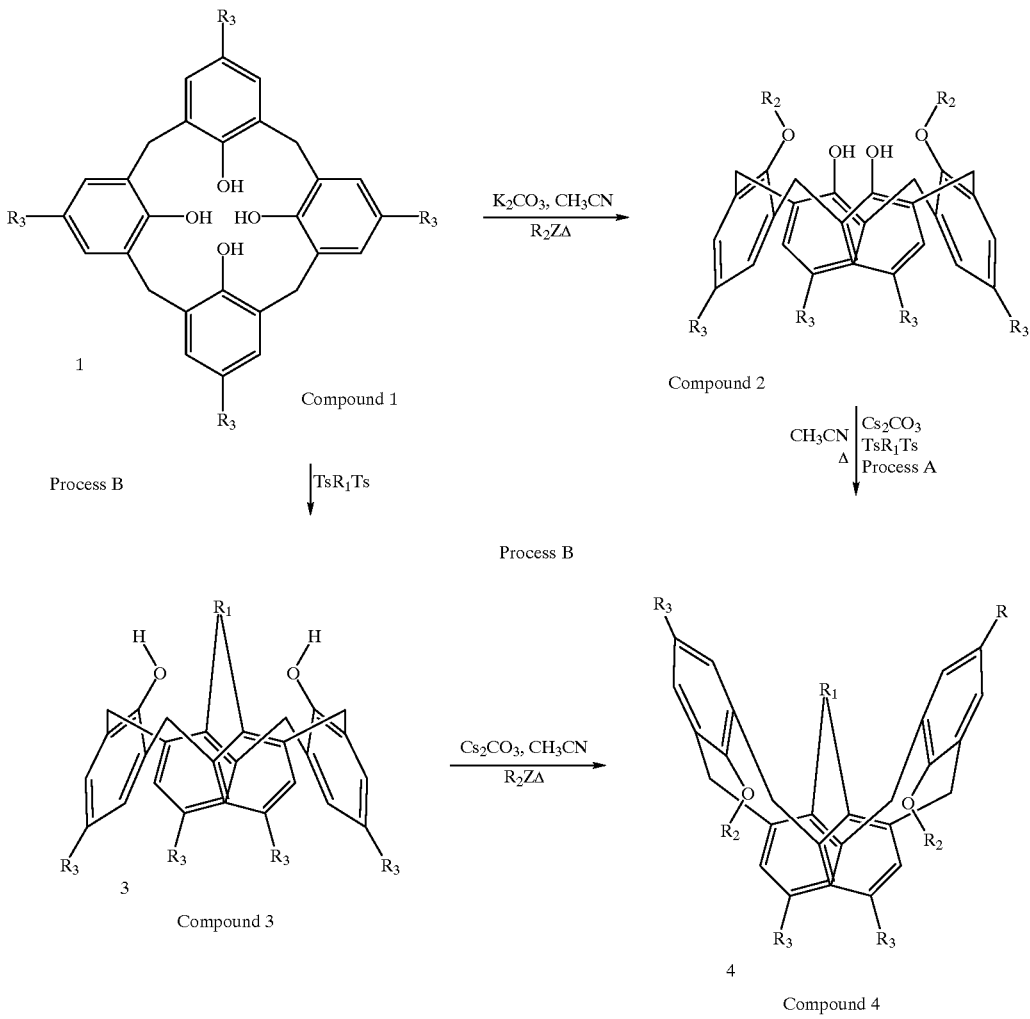

In order to carry out the formation reaction of the bridge $R_1$, the calixarene is dissolved in an appropriate solvent, e.g. in benzene or acetonitrile, to it is added a salt such as potassium carbonate and diparatoluene suphonate of formula (III) or (IV) and refluxing is allowed for an adequate time to form the bridge $R_1$ linking two opposite benzene nuclei. Following the reaction, the reaction mixture is dissolved in an appropriate solvent and the calixarene extracted, e.g. using hydrochloric acid.

In order to carry out the substitution reaction of the calixarene by $R_2$, it is possible to work in a solvent such as acetonitrile, whilst adding potassium carbonate and the halide $R_2Z$, e.g. the iodide.

The crown calix|4|arenes of formula (I) described hereinbefore can in particular be used for the selective extraction of the cesium present in aqueous solutions, particularly acid solutions which may or may not contain sodium, such as dissolving solutions and aqueous effluents from irradiated fuel reprocessing installations.

When the crown calix|4|arene used has alkyl substituents on the benzene nuclei, it can be prepared by a process identical to that described hereinbefore starting with the corresponding substituted calix|4|arene.

A substituted crown calix|4|arene of this type with $R_3$ representing the tert-butyl group is e.g. described by Ghidini et al in J. Am. Chem. Soc., 1990, 112, pp 6979–6985.

For the extraction of the cesium, the aqueous starting solutions can be acid solutions, e.g. nitric solutions containing $10^{-3}$ to 7 mole/l of nitric acid.

To carry said extraction, contacting takes place between the aqueous solution containing the cesium and an immiscible liquid phase comprising the crown calix|4|arene, followed by the recovery of the extracted cesium in the immiscible liquid phase.

This recovery can take place by means of an aqueous solution by contacting the immiscible liquid phase which has extracted the cesium with an aqueous reextraction solution e.g. constituted by distilled and deionized water.

In order to perform this process, it is possible to contact the aqueous solution with the immiscible liquid phase in conventional liquid-liquid extraction installations, such as mixer-settlers, pulsed columns, etc.

This contacting can also take place by having the immiscible liquid phase comprising the crown calix|4|arene in the form of a liquid membrane having two opposite surfaces, the aqueous starting solution containing the cesium being in contact with one of the membrane surfaces, the cesium extracted by the liquid membrane being collected in an aqueous reextraction solution in contact with the opposite membrane surface.

For forming the immiscible liquid phase, the crown calix|4|arene is dissolved in an appropriate solvent. Examples of usable solvents are alkyl benzenes and nitrophenyl alkyl ethers.

Preferably the solvent is constituted by an ether such as ortho-nitrophenylhexylether and ortho-nitrophenyloctylether.

The crown calix|4|arene concentration of the immiscible liquid phase is in particular dependent on the solvent used. It is possible to use concentrations between $10^{-3}$ and $5.10^{-1}$ mole/l, e.g. a concentration of $10^{-2}$ mole/l.

The crown calix|4|arene of formula (I) can also be used for separating certain actinides from trivalent americium. In this case, contacting takes place between the aqueous solution containing the actinides and an immiscible liquid phase containing the crown calix|4|arene in order to selectively extract the actinides whilst keeping the americium in the aqueous solution.

It is pointed out that for the extraction of cesium, as for the extraction of actinides, it is possible to use the calixarenes in the form of pure isomers or isomer mixtures. It is also possible to use mixtures of calixarenes.

Other features and advantages of the invention will become more apparent from reading the following illustrative and non-limitative examples with reference to the attached drawing showing the different ligands used in these examples.

EXAMPLE 1

Preparation of the 6-crown 25, 27-dihydroxycalix|4|arene (compound 4 with $R_1=O(CH_2CH_2O)_5$, $R_2=H$ and $R_3=H$)

In 100 ml of dry benzene is dissolved 1.0 g (2.35 mmole) of calix|4|arene (compound 1 with $R_3=H$). It is refluxed in a nitrogen atmosphere with 0.53 g (4.7 mmole) of potassium tert-butoxide and to it is added dropwise over a period of 6 h a solution containing 1.28 g (2.35 mmole) of pentaethylene glycol di-p-toluene sulphonate in 50 ml of dry benzene.

After 36 h at reflux, the reaction mixture is allowed to cool, is treated with 10% HCl and the separated organic layer is washed twice with water. Finally, the solvent is eliminated under reduced pressure and the residue undergoes chromatography on a silica gel column using as the eluent a hexane/ethyl acetate mixture (1/1). This gives the 6-crown 25, 27-dihydroxycalix|4|arene with a yield of 34%.

The product has the following characteristics:

melting point: 224–225° C.,

NMR of the proton in CDCl$_3$: δ 7.49 (s, 2H, OH), 7.07 (d, 4H, ArH meta, J=7.6 Hz), 6.83 (t, 4H, ArH meta, J=7.6 Hz), 6.70 (t, 2H, ArH, ArH para, J=7.6 Hz), 6.68 (t, 2H, ArH para, J=7.6 Hz), 4.42 (d, 4H, ArCH$_2$Ar, J=13.1 Hz), 4.15 (t, 4H, ArO<u>CH</u>$_2$CH$_2$O (CH$_2$CH$_2$O)$_3$CH$_2$<u>CH</u>$_2$OAr, J=4.8 Hz), 4.01 (t, 4H, ArO<u>CH</u>$_2$CH$_2$O (CH$_2$CH$_2$O)$_3$<u>CH</u>$_2$OAr, J=4.8 Hz), 3.93 (t, 4H, ArOCH$_2$CH$_2$O<u>CH</u>$_2$CH$_2$OCH$_2$ <u>CH</u>$_2$OCH$_2$CH$_2$OCH$_2$CH$_2$OAr, J=4.8 Hz), 3.84 (t, 4H, ArOCH$_2$CH$_2$OCH$_2$<u>CH</u>$_2$OCH$_2$CH$_2$ <u>CH</u>$_2$CH$_2$OCH$_2$CH$_2$OAr, J=4.8 Hz), 3.70 (s, 4H, ArO (CH$_2$CH$_2$O)$_2$<u>CH</u>$_2$<u>CH</u>$_2$O(CH$_2$CH$_2$O)$_2$Ar), 3.36 (d, 4H, ArCH$_2$Ar, J=13.1 Hz).

mass spectrometry (CI) 626.0 (M$^+$ calculated 626.3)

elementary analysis,

| for C$_{38}$H$_{42}$O$_8$ | C | H |
|---|---|---|
| calculated | 72.83 | 6.75 |
| found | 72.71 | 6.91 |

EXAMPLE 2

Preparation of 6-crown 25,27-dimethoxycalix|4|arene (compound 3 with $r_1=O(CH_2CH_2O)_5$, $R_2=CH_3$, $R_3=H$)

Process A

To a solution containing 1.0 g (2.35 mmole) of calix|4|arene (compound 1 with $R_3=H$) in 100 ml of dry acetonitrile is added under a nitrogen atmosphere 0.35 g (2.5 mmole) of potassium carbonate and 0.67 g (4.7 mmole) of iodomethane. The reaction mixture is refluxed for 24 h and then the acetonitrile is eliminated under reduced pressure and the residue is immersed in 100 ml of 10% HCl and 100 ml of dichloromethane. The organic layer is separated, washed twice with distilled water and then the dichloromethane is eliminated by distillation. This is followed by the addition of methanol and the filtration of the precipitate. This gives 1.03 g (2.28 mmole) of a white solid, which is 25,27-dimethoxycalix|4|arene, i.e. compound 2 with $R_2=CH_3$ and $R_3=H$. This solid product is dried under a high vacuum for a few hours and then dissolved in 400 ml of acetonitrile, followed by the addition of 2.93 g (9 mmole) of a cesium carbonate excess and 1.37 g (2.5 mmole) of pentaethylene glycol di-p-toluene sulphonate under a nitrogen atmosphere. The reaction mixture is refluxed for 16 h, then immersed and then treated as hereinbefore. By crystallization of the oily residue in a mixture of dichloromethane/methanol (1/5), 6-crown-25,27-dimethoxycalix|4|arene is obtained (compound 4 with $R_1=O$ (CH$_2$CH$_2$O)$_5$, $R_2=CH_3$ and $R_3=H$) with a total yield of 78%.

This product has the following characteristics:

melting point: 180–181° C.,

NMR of the proton (CDCl$_3$): δ7.15 (d, 4H, ArH meta, J=6.5 Hz), 6.93 (t, 2H, ArH para, J=6.5 Hz), 6.93 (s, 6H, ArH), 4.43 (d, 4H, ArCH$_2$Ar, J=12.9 Hz), 4.05 (s, 4H, O (CH$_2$CH$_2$O)$_2$<u>CH</u>$_2$<u>CH</u>$_2$(OCH$_2$CH$_2$)$_2$O), 3.89 (s, 6H, OCH$_3$), 3.85–3.5 (m, 16H, O(<u>CH$_2$</u> <u>CH$_2$</u>O)$_2$CH$_2$CH$_2$(OCH$_2$—CH$_2$)$_2$O), 3.15 (d, 4H, ArCH$_2$Ar, J=12.9 Hz), mass spectrometry (CI) 6.54.0 (M$^+$ calculated 654.3), elementary analysis

| for C$_{40}$H$_{46}$O$_8$ | C | H |
|---|---|---|
| calculated | 73.37 | 7.08 |
| found | 73.80 | 7.20 |

Process B 0.51 g (0.81 mmole) of the 6-crown-25,27-dihydroxycalix|4|arene prepared in example 1 is dissolved in 200 ml of dry acetonitrile. To this solution is added, accompanied by stirring, 1 g (3.2 mmole) of cesium carbonate and 0.69 g (4.8 mmole) of iodomethane. After 24 h the acetonitrile is eliminated under reduced pressure and the residue is treated with 70 ml of dichloromethane and 70 ml of 10% HCl. The organic phase is separated, washed twice with water and the solvent elimination by distillation. After crystallizing the residue in a mixture of dichloromethane/methanol (1/5), pure 6-crown-25,27-dimethoxycalix|4|arene is obtained (compound 4 with $R_1=O(CH_2CH_2O)_5$, $R_2=CH_3$, $R_3=H$) with a total yield of 33%.

The characteristics of the product obtained are the same as those of the product obtained by process A.

EXAMPLE 3

Preparation of 6-crown-25,27-bis(1-propyloxy)calix|4|arene (compound 4 with $R_1=O(CH_2CH_2O)_5$, $R_2=CH_2CH_2CH_3$ and $R_3=H$).

Process A

To a solution of 1.0 g (2.35 mmole) of calix|4|arene (compound 1 with $R_3=H$) in 100 ml of dry acetonitrile is added 1.30 g (9.4 mmole) of potassium carbonate and 1.60 g (9.4 mmole) of 1-iodopropane under a nitrogen atmosphere. The reaction mixture is refluxed for 36 h, followed by the elimination of the acetonitrile under reduced pressure and the immersion of the residue in 100 ml of 10% HCl and 100 ml of dichloromethane. The organic layer is separated, washed twice with distilled water and then the dichloromethane is eliminated by distillation. Methanol is then added and the precipitate filtered. This gives 1.02 g (2.0 mmole) of a white solid product constituting 25,27-bis(1-propyloxy)calix|4|arene (compound 2 with $R_2$—$CH_2CH_2CH_3$ and $R_3=H$). The solid is then dried under high vacuum for several hours, dissolved in 400 ml of acetonitrile and addition takes place of 2.6 g (8.0 mmole) of a cesium carbonate excess and 1.20 g (2.2 mmole) of pentaethylene glycol di-p-toluene sulphonate under a nitrogen atmosphere. The reaction mixture is refluxed for 16 h, then immersed and treated as described hereinbefore. By crystallizing the oily residue obtained in methanol, 6-crown-25,27-bis(1-propyloxy) calix|4|arene is obtained in pure form (compound 4 with $R_1=O(CH_2CH_2O)_5$, $R_2=CH_2CH_2CH_3$ and $R_3=H$) with a total yield of 64%.

This product has the following characteristics:

melting point: 140–141° C.,

NMR of the proton (CDCl$_3$): δ7.15–6.95 (m, 8H, ArH meta), 6.9–6.6 (m, 4H, ArH para), 3.77–3.33 (m, 32H, O(CH$_2$CH$_2$O)$_5$, O$\underline{CH}_2$CH$_2$CH$_3$, ArCH$_2$Ar), 1.28 (sext, 4H, OCH$_2$$\underline{CH}_2$CH$_3$, J=7.7 Hz), 0.73 (t, 6H, OCH$_2$CH$_2$$\underline{CH}_3$), mass spectrometry (CI) 7.10.2 (M+ calculated 710.4), elementary analysis

| for $C_{44}H_{54}O_8$ | C | H |
|---|---|---|
| calculated | 74.33 | 7.65 |
| found | 74.25 | 7.83 |

Process B 0.51 g (0.81 mmole) of 6-crown-25,27-dihydroxycalix|4|arene (compound 3) prepared in example 1 is dissolved in 200 ml of dry acetonitrile. To this solution is added, accompanied by stirring, 1.06 g (3.2 mmole) of cesium carbonate and 0.82 g (4.8 mmole) of 1-iodopropane. After 24 h elimination takes place of the acetonitrile under reduced pressure and the residue is treated with 70 ml of dichloromethane and 70 ml of 10% HCl. The organic phase is separated, washed twice with water and the solvent eliminated by distillation. By crystallizing in methanol, the pure 6-crown-25,27-bis(1-propyloxy)calix|4|arene is obtained (compound 4 with $R_1=O(CH_2CH_2O)_5$, $R_2=CH_2CH_2CH_3$ and $R_3=H$) with a total yield of 31%.

The characteristics of this product are identical to those of the product obtained by process A.

EXAMPLE 4

Preparation of 6-crown-25,27-bis(2-propyloxy)calix|4|arene (compound 4 with $R_1=O(CH_2CH_2O)_5$, $R_2=CH(CH_3)_2$ and $R_3=H$).

Process A

To a solution of 1.0 g (2.35 mmole) of calix|4|arene (compound 1 with $R_3=H$) and 100 ml of dry acetonitrile is added under a nitrogen atmosphere 0.35 g (2.5 mmole) of potassium carbonate and 1.60 g (9.4 mmole) of 2-iodopropane. The reaction mixture is refluxed for 48 h, the acetonitrile is then eliminated under reduced pressure and the residue immersed in 100 ml of 10% HCl and 100 ml of dichloromethane. The organic layer is separated, washed twice with distilled water and then the dichloromethane is eliminated by distillation. Methanol is then added and the precipitate filtered. The resulting white solid (0.97 g, 1.9 mmole) corresponding to 25, 27-bis(2-propyloxy) calix|4|arene (compound 2 with $R_2=CH(CH_3)_2$ and $R_3=H$) is dried under a high vacuum for several hours and then dissolved in 40 ml of acetonitrile. This is followed by the addition of 2.45 g (7.52 mmole) of a cesium carbonate excess and 1.04 g (1.90 mmole) of pentaethylene glycol di-p-toluene sulphonate under a nitrogen atmosphere. The reaction mixture is refluxed for 16 h, then immersed and treated as described hereinbefore. By crystallization of the oily residue in ethanol pure 6-crown-25,27-(bis-2-propyloxy)calix|4|arene is obtained (compound 4 with $R_1=O(CH_2CH_2O)_5$, $R_2=CH(CH_3)_2$ and $R_3=H$) with a yield of 60%.

This product has the following characteristics:

melting point: 197–198° C., NMR of the proton (CDCl$_3$): δ7.1–7.0 (m, 8H, ArH meta), 6.9–6.7 (m, 4H, ArH para), 4.23 (ept, 2H, O$\underline{CH}$(CH$_3$)$_2$, J=6.3 Hz), 3.8–3.3 (m, 28H, O(CH$_2$CH$_2$O)$_5$, ArCH$_2$Ar), 0.90 (d, 12H, OCH(CH$_3$)$_2$, J=6.3 Hz), mass spectrometry (CI) 710.1 (M$^+$ calculated 710.4), elementary analysis for

| for $C_{44}H_{54}O_8$ | C | H |
|---|---|---|
| calculated | 74.33 | 7.65 |
| found | 74.18 | 7.19 |

EXAMPLE 5

Preparation of 7-crown-25,27-dimethoxycalix|4|arene (compound 4 with $R_1=O(CH_2CH_2O)_6$, $R_2=CH_3$, $R_3=H$ Process A To a solution of 1.0 g (2.35 mmole) of calix|4|arene (compound 1 with $R_3=H$) in 100 ml of dry acetonitrile is added under a nitrogen atmosphere 3.06 g (2.5 mmole) of potassium carbonate and 0.67 g (4.7 mmole) of iodomethane. The reaction mixture is refluxed for 24 h and then the acetonitrile is eliminated under reduced pressure, followed by the immersion of the residue in 100 ml of 10% HCl and 100 ml of dichloromethane. The organic layer is separated, washed twice with distilled water and the dichloromethane is eliminated by distillation. Methanol is then added and the precipitate filtered. The resulting white solid (1.03 g, 2.28 mmole) corresponding to 25, 27-dimethoxycalix|4|arene (compound 2 with $R_2=CH_3$ and $R_3=H$) is dried under high vacuum for several hours and then dissolved in 400 ml of acetonitrile. This is followed by the addition under a nitrogen atmosphere of 2.97 g (9 mmole) of a cesium carbonate excess and 1.48 g (2.5 mmole) of hexaethylene glycol di-p-toluene sulphonate. The reaction mixture is refluxed for 16 h, immersed and treated as described hereinbefore. By crystallizing the oily residue in a mixture of dichloromethane/methanol (1/5), pure 7-crown-25,27-dimethoxycalix|4|arene is obtained (compound 4 with $R_1=O(CH_2CH_2O)_6$, $R_2=CH_3$ and $R_3=H$) having a total yield of 75%.

The product has the following characteristics:

melting point: 121–122-C.,

NMR of the proton ($CDCl_3$): δ7.4–6.7 (m, 8H, ArH), 6.6–6.35 (m, 4H, ArH), 4.50 (d, 4H, $ArCH_2Ar$, J=13.0 Hz), 4.02–3.10 (m, 34H, $O(CH_2CH_2O)_6$, $OCH_3$, $ArCH_2Ar$, mass spectrometry (CI) 698.0 ($M^+$ calculated 698.3), elementary analysis for

| for $C_{42}H_{50}O_9$ | C | H |
| --- | --- | --- |
| calculated | 72.18 | 7.21 |
| found | 71.96 | 7.43 |

EXAMPLE 6

Preparation of 6-crown-25,27-bis(1-octyloxy)calix|4|arene (compound 4 with $R_1=O(CH_2CH_2O)_5$, $R_2=(CH_2)_7CH_3$ and $R_3=H$).

Process A

To a solution of 1.0 g (2.35 mmole) of calix|4|arene (compound 1 with $R_3=H$) in 100 ml of dry acetonitrile is added under a nitrogen atmosphere 0.75 g (5.4 mmole) of potassium carbonate and 0.99 g (5.17 mmole) of 1-bromooctane. The reaction mixture is refluxed for 6 days and then the acetonitrile is eliminated under reduced pressure and the residue immersed in 100 ml of 10% HCL and 100 ml of dichloromethane. The organic layer is separated, washed twice with distilled water, the dichloromethane eliminated by distillation and the residue treated with cold petroleum ether. The resulting white solid (0.70 g, 1.08 mmole) corresponding to 25.27-bis(1,octoyloxy)calix|4|arene (compound 2 with $R_2=(CH_2)_7CH_3$ and $R_3=H$) is dried under a high vacuum for several hours and then dissolved in 400 ml of acetonitrile. This is followed by the addition of 1.40 g (4.3 mmole) of a cesium carbonate excess and 0.65 g (1.19 mmole) of pentaethylene glycol di-p-toluene sulphonate under a nitrogen atmosphere. The reaction mixture is refluxed for 16 h, immersed and treated as hereinbefore. By silica gel column chromatography of the oily residue obtained, using as the eluent a mixture of hexane and ethyl acetate (1/1) and crystallization in methanol, pure 6-crown-25,27-bis(1-octyloxy)calix|4|arene is obtained (compound 4 with $R_1=O(CH_2CH_2O)_5$, $R_2=(CH_2)_7CH_3$ and $R_3=H$) with a total yield of 35%.

This product has the following characteristics:

melting point: 94–95° C.,

NMR of the proton ($CDCl_3$): 7.12 (d, 4H, ArH meta, J=7.5 Hz), 7.08 (d, 4H, ArH meta, J=7.5 Hz), 6.83 (t, 2H, ArH para, J=7.5 Hz), 6.77 (t, 2H, ArH para, J=7.5 Hz), 3.78 (s, 8H, $ArCH_2Ar$), 3.71 (s, 4H, $O(CH_2CH_2O)_2\underline{CH_2CH_2}(OCH_2CH_2)_2O$), 3.66, 3.60, 3.49 and 3.40 (t, every 4H, $O(\underline{CH_2CH_2}O)_2CH_2CH_2(O\underline{CH_2CH_2})_2O$), 3.43 (5, 4H, $O\underline{CH_2}(CH_2)_6CH_3$, J=7.4 Hz), 1.36–1.15 (m, 24H, $OCH_2(\underline{CH_2})_6CH_3$), 0.92 (t, $OCH_2(CH_2)_6CH_3$, J=7.1 Hz), mass spectrometry (CI) 850.2 ($M^+$ calculated 850.5), elementary analysis for

| for $C_{54}H_{74}O_8$ | C | H |
| --- | --- | --- |
| calculated | 76.20 | 8.76 |
| found | 76.02 | 8.86 |

EXAMPLE 7

Preparation of 6-crown-25,27-bis(ethoxycarbonylmethoxy)calix|4|arene (compound 4 with $R_1=O(CH_2CH_2O)_5$, $R_2=CH_2COOCH_2CH_3$ and $R_3=H$).

Process A

To a solution of 1.0 g (2.35 mmole) of calix|4|arene (compound 1 with $R_3=H$) in 100 ml of dry acetonitrile is added under a nitrogen atmosphere 0.36 g (2.6 mmole) of potassium carbonate and 0.82 g (4.94 mmole) of ethyl monobromoacetate. The reaction mixture is refluxed for 24 h, then the acetonitrile is eliminated under reduced pressure and the residue immersed in 100 ml of 10% HCl and 100 ml of dichloromethane. The organic layer is separated, washed twice with distilled water and the dichloromethane eliminated by distillation. The residue is treated with methanol and the precipitate filtered. The resulting white solid (1.26 g, 2.12 mmole) corresponding to 25,27-bis(ethoxycarbonylmethoxy)calix|4|arene (compound 2 with $R_2=CH_2COOCH_2CH_3$), $R_3=H$) is dried under a high vacuum for several hours and then dissolved in 400 ml of acetonitrile. Under a nitrogen atmosphere addition takes place of 2.76 g (8.46 mmole) of a cesium carbonate excess and 1.28 g (2.33 mmole) of pentaethylene glycol di-p-toluene sulphonate. The reaction mixture is refluxed for 16 h, immersed and treated as hereinbefore. By silica gel column chromatography of the oily residue using as the eluent ethyl acetate, the pure 6-crown-25,27-bis(ethoxycarbonylmethoxy)calix|4|arene is obtained (compound 4 with $R_2=CH_2COOCH_2CH_3$ and $R_3=H$) with a total yield of 45% in the form of a vitreous product.

The product has the following characteristics:

NMR of the proton ($CDCl_3$): δ7.12 (d, 8H, ArH meta, J=7.2 Hz), 6.89 (t, 2H, ArH para), 6.80 (t, 2H, ArH para), 4.3–3.3 (m, 36H, $ArCH_2Ar$, $O(CH_2CH_2O)_5$, $O\underline{CH_2}COO\underline{CH_2}CH_3$), 1.20 (t, 6H, $OCH_2\underline{CH_3}$, J=7.6 Hz)

$^{13}C$ NMR ($CDCl_3$): δ170.1 (s, C=O), 157.0 and 155.3 (s, ArO), 134.6 and 133.8 (s, Ar, ortho), 130.4 (d, Ar meta), 123.1 and 122.8 (d, Ar para), 7.1.1, 70.9, 70.6, 70.0, 69.3, 68.2 (t, $O\underline{CH_2CH_2}O)_5$ and $O\underline{CH_2}CO$), 60.22 (t, $O\underline{CH_2}CH_3$), 37.9 (t, $ArCH_2Ar$), 14.1 (q, $OCH_2CH_3$), mass spectrometry (CI) 798.1 ($M^+$ calculated 798.4), melting point 65–66° C., elementary analysis for

| for $C_{46}H_{54}O_{12}$ | C | H |
| --- | --- | --- |
| calculated | 69.16 | 6.81 |
| found | 68.97 | 6.96 |

EXAMPLE 8

Preparation of 6-crown-25,27-bis(2-hydroxyethoxy)-calix|4|arene (compound 4 with $R_1=O(CH_2CH_2O)_5$, $R_2=CH_2CH_2OH$ and $R_3=H$).

Dissolving takes place in 50 ml of dry tetrahydrofuran of 1.06 mmole of 6-crown-25,27-bis(ethoxycarbonylmethoxy) calix|4|arene prepared in example 7 (compound 4 with $R_1=O(CH_2CH_2O)_5$, $R_2=CH_2COOCH_2CH_3$ and $R_3=H$) and to the solution is added 0.16 g (4.24 mmole) of $LiAlH_4$.

After stirring for 2 hours at ambient temperature, the tetrahydrofuran is eliminated by distilling under reduced pressure. The residue is then treated with 50 ml of ethyl acetate and 50 ml of 10% HCl and the organic phase is washed twice with water. The ethyl acetate is eliminated and the residue crystallized in methanol to obtain 6-crown-25,27-bis(2, hydroxyethyoxy)calix|4|arene (compound 4 with $R_1$=O $(CH_2CH_2O)_5$, $R_2$=$CH_2CH_2OH$ and $R_3$=H) with a reduction yield of 95%.

The product obtained has the following characteristics:
melting point 154–155° C., NMR of the proton (CDCl$_3$): 7.15–7.10 (m, 8H, ArH meta), 6.95–6.90 (m, 4H, ArH para), 3.87 (s, 8H, ArCH$_2$Ar), 3.71 (s, 4H, O(CH$_2$CH$_2$O)$_2$CH$_2$ CH$_2$(OCH$_2$CH$_2$)$_2$O), 3.67, 3.65, 3.52 and 3.40 (t, every 4H, O(CH$_2$CH$_2$O)$_2$CH$_2$CH$_2$ (OCH$_2$CHO2)$_2$O), 3.60 (t, 4H, OCH$_2$CH$_2$OH, J=6.7 Hz), 3.17 (m, 4H, O CH$_2$CH$_2$OH, J=6.7 Hz), 2.38 (t, 2H, OCH$_2$CH$_2$OH), mass spectrometry (CI) 714.0 (M$^+$ calculated 7.14.4), elementary analysis for

| for $C_{42}H_{50}O_{10}$ | C | H |
| --- | --- | --- |
| calculated | 70.57 | 7.05 |
| found | 70.39 | .23 |

EXAMPLES 9 TO 14
Cesium Extraction.

In these examples extraction takes place of the cesium present in an aqueous solution with a nitric acid concentration of 1 mole/l and containing 5.10$^{-4}$ mole/l of CsNO$_3$.

For this purpose one volume of aqueous solution is contacted with one volume of organic liquid constituted by ortho-nitrophenyl hexyl ether containing 10$^2$ mole/l of organic extractant. When equilibrium is reached, measurement takes place by gamma spectrometry of the cesium content of the organic liquid. The cesium percentage extracted is then determined, together with the distribution coefficient $D_{Cs}$ corresponding to the ratio of the cesium concentration in the organic liquid to the cesium concentration of the aqueous solution at equilibrium.

In these examples, the organic extractant is constituted by the macrocyclic ligands of table 1, whose formula are given in the attached drawing. The results obtained are also given in table 1.

In these examples, examples 9 to 12 relate to the use of the calix|4|arenes of the invention, whereas examples 13 and 14 are given for comparison purposes and illustrate the use of crown ethers as extractants.

The results of table 1 show that the calixarenes used in examples 10 and 11 (calixarenes of examples 3 and 4) make it possible to obtain very high extraction rates. Moreover, the cesium extracted in said example can be recovered by contacting the organic phase with demineralized water.

EXAMPLES 15 TO 19
Strontium Extraction.

One starts with an aqueous solution having a nitric acid concentration of 1 mole/l and containing 5.10 mole/l of strontium nitrate and it undergoes an extraction under the same conditions as in examples 9 to 14 using an organic liquid phase constituted by orthonitrophenyl hexyl ether containing 10$^{-2}$ mole/l of macrocylic extractant.

This is followed by the measurement of the strontium content of the organic phase by gamma spectrometry and the extracted strontium percentage and the distribution coefficient $D_{Sr}$ are determined. The extractants used and the results obtained are given in table 2.

EXAMPLES 20 TO 25
Sodium Extraction.

In these examples, one starts with an aqueous solution having a nitric acid concentration of 1 mole/l containing 5.10 mole/l of sodium nitrate and it is subject to an extraction under the same conditions as in examples 9 to 14 using a macrocyclic extractant with a concentration of 10 mole/l in orthonitrophenyl hexyl ether. As previously, the sodium content of the organic solution is measured by gamma spectrometry and the extracted sodium percentage and distribution coefficient $D_{Na}$ are evaluated. The extractants and results obtained are given in table 3.

The results given in tables 1 to 3 show that the crown calix|4|arenes used in the invention extract cesium with good yields and separate it from the sodium and strontium also present in the effluents from reprocessing installations.

On the basis of the results of tables 1 to 3, it is possible to calculate the selectivities of the different extractants with respect to these cations in a nitric medium.

Thus, the following values are obtained for the selectivity (Cs/Na)=$D_{Cs}/D_{Na}$ relative to cesium and compared with sodium:

6-crown-25,27-dimethoxy calix|4|arene: 14
6-crown-25,27-bis(1-propyloxy)calix|4|arene: 10$^4$
6-crown-25,27-bis(2-propyloxy)calix|4|arene: 7.10$^4$
whereas this selectivity is 250 for the crown ether B21C7.

For the selectivity Cs/Sr relative to cesium compared with strontium, the following values are obtained:

6-crown-25,27-dimethoxy-calix|4|arene: ≧40,
6-crown-25,27-bis(1-propyloxy)calix|4|arene: ≈10$^5$,
6-crown-25,27-bis(2-propyloxy)calix|4|arene: ≈8.10$^4$
whereas this selectivity is only 7.6.10$^{-2}$ for the crown ether DCH18C6.

This is why the calixarenes according to the invention make it possible to obtain selective transports of cesium 137 in the trace state in a matrix of 4M sodium nitrate and 1M nitric acid containing other fission products such as Sr 90 (simulated by $^{85}$Sr) also in the trace state.

The results of tables 1 to 3 also show that the calix|4|arenes of the invention are very good cesium extractants. This selectivity peak could be explained by a good adequation between the size of the available cavities and the size of the extracted cation.

EXAMPLES 26 TO 30
Actinide Extraction.

In these examples, one starts with an aqueous solution containing 1 mole/l of nitric acid and 4 mole/l of sodium nitrate, containing traces of Np 237, Pu 239 and Am 241. The actinides are extracted using a liquid organic phase constituted by a macrocyclic extractant at a concentration of 10$^{-2}$ mole/l in orthonitrophenyl octyl ether or orthonitrophenyl hexyl ether, or a known extractant (CMPO) at a concentration of 10$^{-2}$ mole/l in orthonitrophenyl hexyl ether.

This is followed by the measurement of the $^{237}$Np, $^{239}$Pu and $^{241}$AM quantities present in the organic solution and the distribution coefficients of neptunium, plutonium and americium between the two contacting phases are determined. The extractants used and the results obtained are given in table 4.

These results show that the crown calix|4|arenes according to the invention are not such good extractants as CMPO, but are more selective, because they do not extract trivalent americium.

Thus, with 6-crown,25,27-diisopropoxy calix|4|arene transport experiments can be carried out by placing the organic liquid phase in the form of a liquid membrane separating the starting aqueous solution from a reextracion solution constituted by demineralized water and decontaminating more than 90% Pu 239 and more than 45% Np 237 in less than 96 h without transporting americium.

The crown calix|4|arenes according to the invention can also be used in analysis, e.g. for determining the activity of the different isotopes of cesium, particularly Cs-135. They can also be used in detoxification.

TABLE 1

| Example | Organic Extractant | Cs Extracted (in %) | $D_{Cs}$ |
|---|---|---|---|
| 9 | 6-crown-25,27-dimethoxycalix|4|arene | 3.78 | 0.039 |
| 10 | 6-crown-25,27-bis(1-propyloxy)calix|4|arene | 95 | 19.15 |
| 11 | 6-crown-25,27-bis(2-propyloxy)calix|4|arene | 96.6 | 28.5 |
| 12 | 7-crown-25,27-dimethoxycalix|4|arene | 0.7 | $7.10^{-3}$ |
| 13 | 7-crown-21-decylbenzo-(decB21C7) | 24 | 0.33 |
| 14 | 6-crown-18-dicyclohexano-(DCH18C6) | 1.9 | $1.9 \cdot 10^{-2}$ |

TABLE 2

| Example | Organic Extractant | Sr Extracted (in %) | $D_{Sr}$ |
|---|---|---|---|
| 15 | 6-crown-25,27-dimethoxycalix|4|arene | $\leq 0.1$ | $\leq 10^{-3}$ |
| 16 | 6-crown-25,27-bis(1-propyloxy)calix|4|arene | $\approx 0.02$ | $\approx 2.10^{-4}$ |
| 17 | 6-crown-25,27-bis(2-propyloxy)calix|4|arene | $\approx 0.035$ | $\approx 3.5 \cdot 10^{-4}$ |
| 18 | 7-crown-25,27-dimethoxy calix|4|arene | $\leq 0.01$ | $\leq 10^{-4}$ |
| 19 | 6-crown-18-dicyclohexano-(DCH18C6) | 20 | 0.25 |

TABLE 3

| Example | Organic Extractant | Na Extracted (in %) | $D_{na}$ |
|---|---|---|---|
| 20 | 6-crown-25,27-dimethoxycalix|4|arene | 0.27 | $2.7 \cdot 10^{-3}$ |
| 21 | 6-crown-25,27-bis(1-propyloxy)calix|4|arene | 0.18 | $1.8 \cdot 10^{-3}$ |
| 22 | 6-crown-25,27-bis(2-propyloxy)calix|4|arene | 0.04 | $4.10^{-4}$ |
| 23 | 7-crown-25,27-dimethoxycalix|4|arene | 0.38 | $3.8 \cdot 10^{-3}$ |
| 24 | 7-crown-21-decylbenzo (decB21C7) | 0.13 | $1.3 \cdot 10^{-3}$ |
| 25 | 6-crown-18-dicyclohexane (DCH18C6) | 0.47 | $4.7 \cdot 10^{-3}$ |

TABLE 4

| Example | Organic Extractant | $D_{Np}^{237}$ | $D_{Pu}^{239}$ | $D_{Am}^{241}$ |
|---|---|---|---|---|
| 26 | 6-crown-25,27-dimethoxycalix|4|arene (1) | 0.02 | 0.06 | $3.10^{-3}$ |
| 27 | 6-crown-25,27-bis(-propyloxy)calix|4|arene (1) | 0.09 | 10 | $3.10^{-3}$ |
| 28 | 6-crown-25,27-bis(2-propyloxy)calix|4|arene (1) | 0.18 | 14.5 | $4.10^{-3}$ |
| 29 | 7-crown-25,27,dimethoxycalix|4|arene | 0.05 | 1.7 | $4.10^{-3}$ |
| 30 | CMPO (2) | 0.85 | 22 | 1.2 |

(1) In orthonitrophenyl octyl ether: O-NPOE
(2) In orthnitrophenyl hexyl ether: D-NPHE

We claim:

1. Crown calix|4|arene of formula:

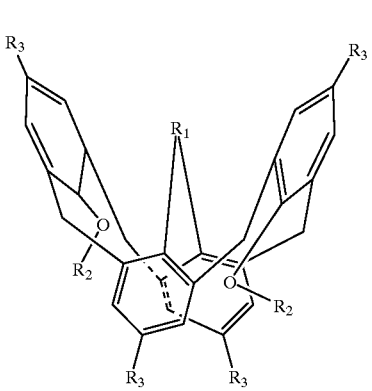

(I)

in which $R_1$ represents a group of formula $X(CH_2CH_2X)_m$ or formula $X(CH_2CH_2X)_n YX (CH_2CH_2X)_n$ in which X represents 0, Y a cycloalkylene group having 6 to 12 carbon atoms or an arylene group selected from the group consisting of phenylene, naphthalene, benzylene, pyridylene and thienylene, m being equal to 3, 4, 5 or 6 and n equal to 1, 2 or 3, $R_2$ represents a hydrogen atom, an alkyl group having 1 to 12 carbon atoms, a group of formula

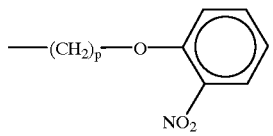

with p being equal to 5, 6, 7 or 8, —$CH_2$—$CH_2OH$ or —$CH_2COR_5$ with $R_5$ representing a group of formula $OR_6$, $NR_6R_7$ or $R_{61}$, in which $R_6$ and $R_7$, which can be the same or different, represent a hydrogen atom, an alkyl group having 1 to 4 carbon atoms or an aryl group having 6 to 14 carbon atoms, the two $R_2$ possibly being different, and $R_3$ represents a hydrogen atom or a $C_1$ to $C_3$ alkyl group.

2. Crown calix|4|arene according to claim 1, wherein $R_1$ represents $O(CH_2CH_2O)_m$ with m being equal to 5 or 6.

3. Crown calix[\v]4|arene according to claim 1, wherein $R_3$ represents a hydrogen atom.

4. Crown calix|4|arene according to claim 1, wherein $R_2$ represents an alkyl group with 1 to 8 carbon atoms, $CH_2COOCH_3$ or $CH_2CH_2OH$.

5. Crown calix|4|arene according to claim 1, wherein $R_1$ represents $O(CH_2CH_2O)_5$, $R_2$ represents $-CH_2CH_2CH_3$ or $-CH(CH_3)_2$ and $R_3$ represents a hydrogen atom.

6. Process for the preparation of a crown calix|4|arene according to formula (I) of claim 1 with $R_2$ being a hydrogen atom, wherein it consists of reacting a calix|4|arene of formula:

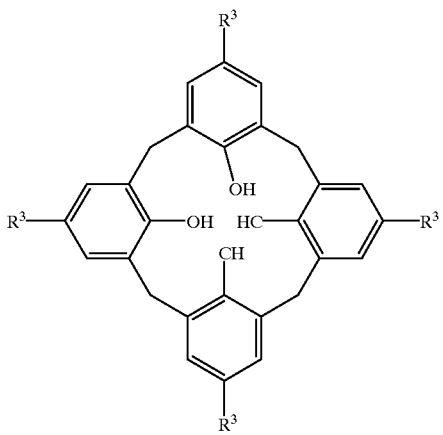

(II)

in which $R_3$ has the meaning given in claim 1 with a compound complying with one of the following formulas:

$$TsX(CH_2CH_2X)_mTs \qquad (III)$$

and $$TsX(CH_2CH_2X)_nYX(CH_2CH_2X)_nTs \qquad (IV)$$

in which X, M, Y and n have the meanings given in claim 1 and Ts represents $CH_3-C_6H_4-SO_2$ and separating the crown calix|4|arene obtained from the reaction medium.

7. Process for the preparation of a crown calix|4|arene according to formula (I) of claim 1 with $R_2$ being different from H, wherein it comprises the following stages:

a) reacting the calix|4|arene of formula:

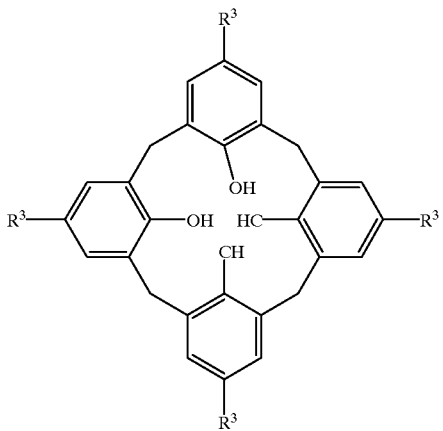

(II)

in which $R_3$ has the meaning given in claim 1 with a compound complying with one of the following formulas:

$$TsX(CH_2CH_2X)_mTs \qquad (III)$$

and $$TsX(CH_2CH_2X)_nYX(CH_2CH_2X)_nTs \qquad (IV)$$

in which X, m, Y and n have the meanings given in claim 1 and Ts represents $CH_3-C_6H_4-SO_2$, b) reacting the crown calix|4|arene obtained in stage a) with a halide of formula $R_2Z$, in which $R_2$ has the meaning given in claim 1 and Z is a halogen atom and c) separating the crown calix|4|arene of formula (I) obtained in this way from the reaction medium.

8. Process for the preparation of a crown calix|4|arene according to formula (I) of claim 1 with $R_2$ different from H, wherein it comprises the following stages:

a) reacting a calix|4|arene of formula:

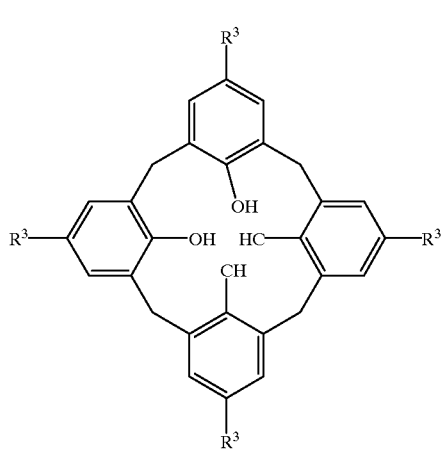

(II)

in which $R_3$ has the meaning given in claim 1, with a halide of formula $R_2Z$, in which $R_2$ has the meaning given in claim 1 and Z is a halogen atom, b) reacting the calix|4|arene obtained in stage a) with a compound complying with one of the following formulas:

$$TsX(CH_2CH_2X)_mTs \qquad (III)$$

and $$TsX(CH_2CH_2X)_nYX(CH_2CH_2X)_nTs \qquad (IV)$$

in which X, m, Y and n have the meanings given in claim 1 and Ts represents $Ch_3-C_6H_4-SO_2$ and c) separating the crown calix|4|arene obtained from the reaction medium.

9. Process for separating cesium from an aqueous solution, wherein it consists of contacting said aqueous solution with an immiscible liquid phase incorporating a crown calix|4|arene according to claim 1 or 5 and then recovering the cesium extracted in said liquid phase.

10. Process according to claim 9, wherein the cesium is ten extracted in an aqueous reextraction solution by contacting the liquid phase which has extracted the cesium with an aqueous solution.

11. Process according to claim 10, wherein the aqueous reextraction solution is distilled and deionized water.

12. Process according to claim 10, wherein the immiscible liquid phase forms a liquid membrane and in that the cesium-containing aqueous solution is contacted with one surface of said membrane and the aqueous reextraction solution is contacted with the opposite surface of said liquid membrane.

13. Process according to claim 9, wherein the aqueous starting solution is an aqueous, cesium-containing effluent, with or without sodium and/or strontium obtained from an irradiated fuel reprocessing installation.

14. Process for separating the actinides and trivalent americium present in an aqueous solution, wherein it consists of contacting said aqueous solution with an immiscible liquid phase incorporating a crown calix|4|arene according to claim 1 or 5 and then recovering the extracted actinides in the immiscible liquid phase.

* * * * *